March 12, 1968 W. FLEMER III Plant Pat. 2,801
CRAB APPLE TREE
Filed Dec. 22, 1966
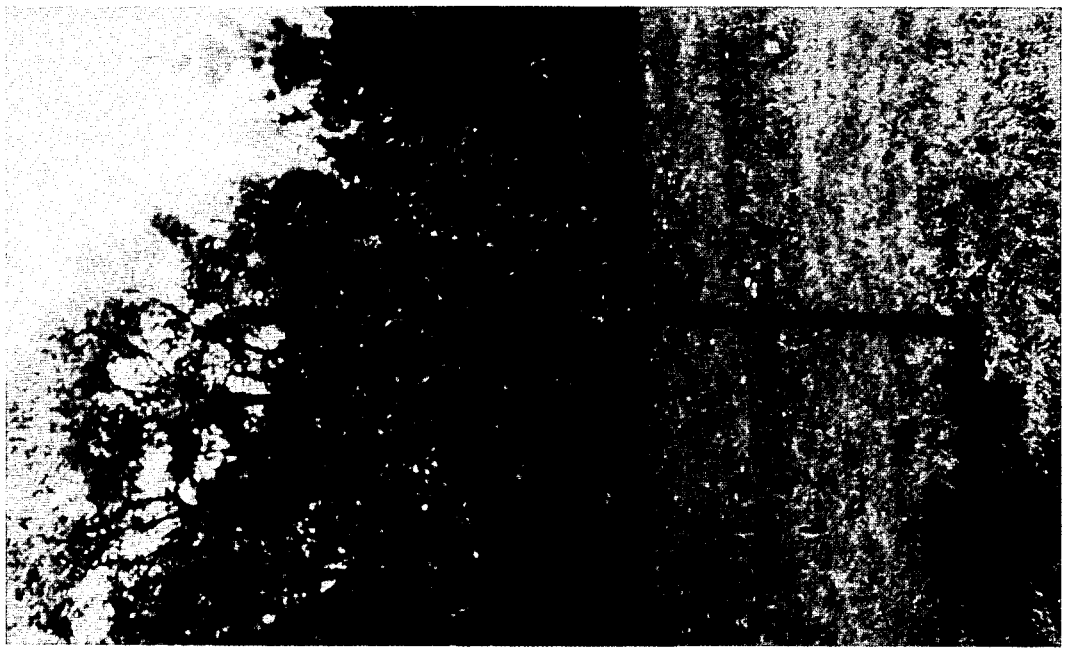
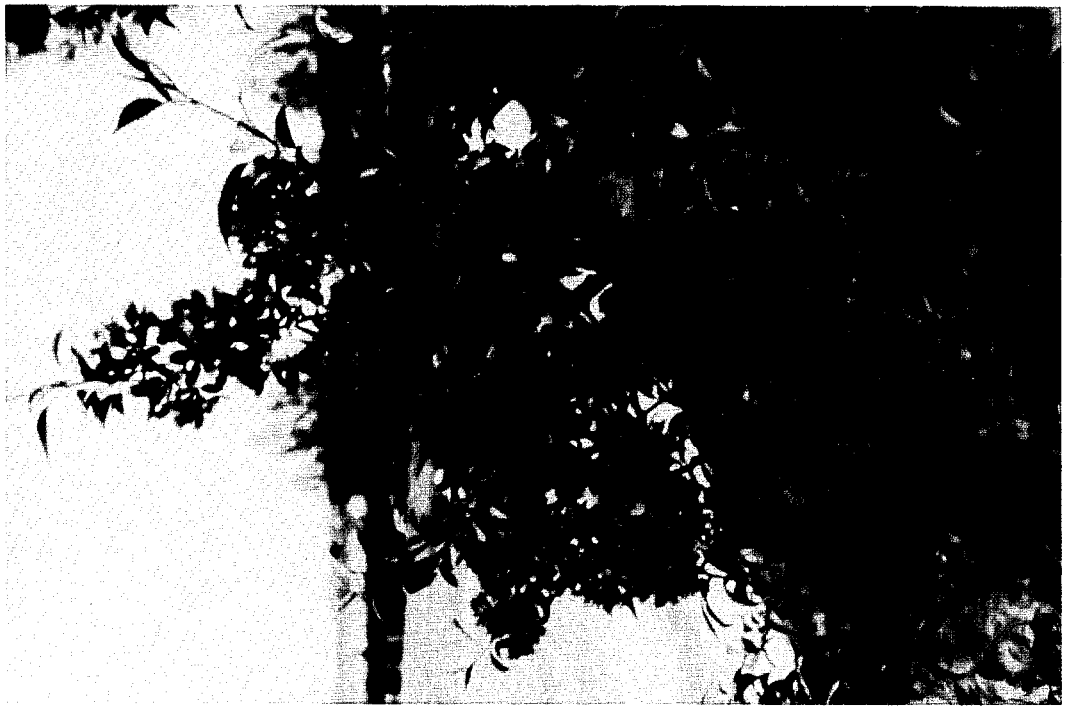
Inventor.
William Flemer, III
By: Robb & Robb
Attorneys.

United States Patent Office

Plant Pat. 2,801
Patented Mar. 12, 1968

2,801
CRAB APPLE TREE

William Flemer III, Princeton, N.J., assignor to Treesearch, Kingston, N.J., a partnership Filed Dec. 22, 1966, Ser. No. 604,076
1 Claim. (Cl. Plt.—34)

The present invention relates to a new and distinct variety of flowering crab apple tree which was originated by me by crossing an unnamed and unpatented variety of the species botanically known as *Malus baccata*, with the variety known as Malus "Katherine" (unpatented).

As the result of this breeding, I have produced a new and improved variety of flowering crab apple tree which is distinguished from its parents, as well as from all other varieties of which I am aware, as evidenced by the following unique combination of characteristics which are outstanding therein:

(1) Good winter hardiness, with no winter die-back at terminals of twigs of young plants even when extended growing seasons produce late growth of such twigs, there being die-back of such growth in other varieties; and (2) A distinctive, attractive and unusually sharp, clear Crimson Red color of the flowers, with a Scarlet overlay free from unattractive Magenta or muddy tints characteristic of other so-called red flowered crab apple varieties.

The accompanying drawing shows a typical young tree specimen of my new variety, and typical flowers as depicted on a somewhat enlarged scale, all as depicted in color as nearly true as it is reasonably possible to make the same in a color illustration of this character.

The following is a detailed description of my new variety, with color terminology in accordance with the Munsell Color Chart, except where general color terms of ordinary dictionary significance are obvious:

Parentage: Seedling.
- *Seed parent.*—An unnamed variety of the species botanically known as *Malus baccata.*
- *Pollen parent.*—Malus "Katherine."

Locality where grown and observed: Plainsboro Township, N.J.

Tree: Small; spreading; dense; hardy.
- *Trunk.*—Slender.
- *Branches.*—Slender; smooth. Lenticels—moderately few; small; round.

- *Color.*—Moderate Reddish Brown, Plate 10R 3/4.

Foliage:
- *Leaves*—Moderately abundant. Length—from 6 cm. to 7 cm. Width from 3 cm. to 3.5 cm. Shape—elliptic oblong; acuminate; cuneate. Color.—young leaves—Moderate Reddish Brown, Plate 7.5R 3/6; mature leaves—Bronze Green, Plate 10YR 3/1. Margin—serrate; sub-lobate on some leaves, and if so, usually 1 lobe about 0.5 cm. deep. Petiole—short (about 1.5 cm. long).

Glands—none. Stipules—from 0.6 cm. to 0.7 cm. long.

Flower buds (when dormant): Very hardy; very small, about 0.28 cm. long; ovate. Color—brown.

Flowers (in central New Jersey):
- *Blooming season.*—First bloom—about May 10. Full bloom—about May 14.
- *Quantity.*—Very abundant.
- *Size.*—Medium; from 4.0 cm. to 4.3 cm. in diameter.
- *Petalage.*—Single; 5 petals per flower. Petals—about 2 cm. long and about 1 cm. wide.
- *Color.*—Buds—Strong Red, Plate 5R 4/12. Open flowers—Clear Strong Red, Plate 5R 4/12 overlaid with Scarlet, Plate 7.5R 4/11.

Fruit: Borne in fall; small; ovoid.
- *Length.*—About 1.2 cm.
- *Width.*—About 0.9 cm.
- *Length of petiole*—About 1.5 cm.
- *Color.*—Dark Red, Plate 5R 3/7.

I claim:

A new and distinct variety of flowering crab apple tree, substantially as herein shown and described, characterized particularly as to novelty by the unique combination of good winter hardiness, with no winter die-back at terminals of twigs of young plants even when extended growing seasons produce late growth of such twigs, there being die-back of such growth in other varieties and a distinctive, attractive and unusually sharp, clear Crimson Red color of the flowers, with a Scarlet overlay free from unattractive Magenta or muddy tints characteristic of other so-called red flowered crab apple varieties.

No references cited.

ROBERT E. BAGWILL, *Primary Examiner.*